May 1, 1956 G. MERRILL Plant Pat. 1,473

PEACH TREE

Filed March 18, 1955

WITNESS

Addison E. Avery

INVENTOR

Grant Merrill

Webster & Webster

ATTYS.

United States Patent Office

Plant Pat. 1,473
Patented May 1, 1956

1,473

PEACH TREE

Grant Merrill, Red Bluff, Calif.

Application March 18, 1955, Serial No. 495,365

1 Claim. (Cl. 47—62)

This invention relates to a new and distinct variety of peach tree which is of moderate vigor, and a regular bearer of large, freestone fruit whose skin is of a yellow under-color with an attractive red blush, and whose flesh is yellow, mottled with red next to the stone.

A major distinguishing characteristic of the instant variety of peach tree is that it bears fruit which has a relatively late ripening period, yet the flesh does not contain any of the greenness common to many other late ripening varieties of peaches.

In comparison to the Merrill Fiesta peach (United States Plant Patent No. 1099), which the present variety most nearly resembles, the fruit here ripens usually about twenty days later, although it does not have quite as much exterior color.

In comparison to the Elberta peach (unpatented), the fruit of the present variety ripens usually about sixty days later.

Additional distinguishing characteristics of the present variety are that the fruit is relatively juicy for a late ripening peach, and such fruit—when eating ripe—has little of the mealiness present in many other late ripening varieties of peaches.

Other distinguishing characteristics of the fruit of the present variety are that it sizes very easily; is firm and remains so for shipping; is pleasing in flavor; and does not oxidize and darken upon exposure to air, which is desirable for late canning or freezing use.

The present variety of peach tree is a seedling which resulted from an open-pollinated cross between the sterile Merrill Rodeo peach (United States Plant Patent No. 1097) and an unknown male parent. Seeds of this cross were gathered by me and a number of such seeds were planted in my orchard near Red Bluff, Tehama County, California. The seedlings, from such planting, were maintained under careful observation, and when such seedlings came into bearing one was recognized as being very distinct in that it had a relatively late ripening period. Such one seedling, which is the present variety, was thus selected by me for further testing and reproduction.

The variety was asexually reproduced by budding onto mature Golden Jubilee (unpatented) peach trees in my orchard located as aforesaid. When these asexual reproductions came into bearing they were found to correspond in all respects to the parent seedling.

Figure 1:
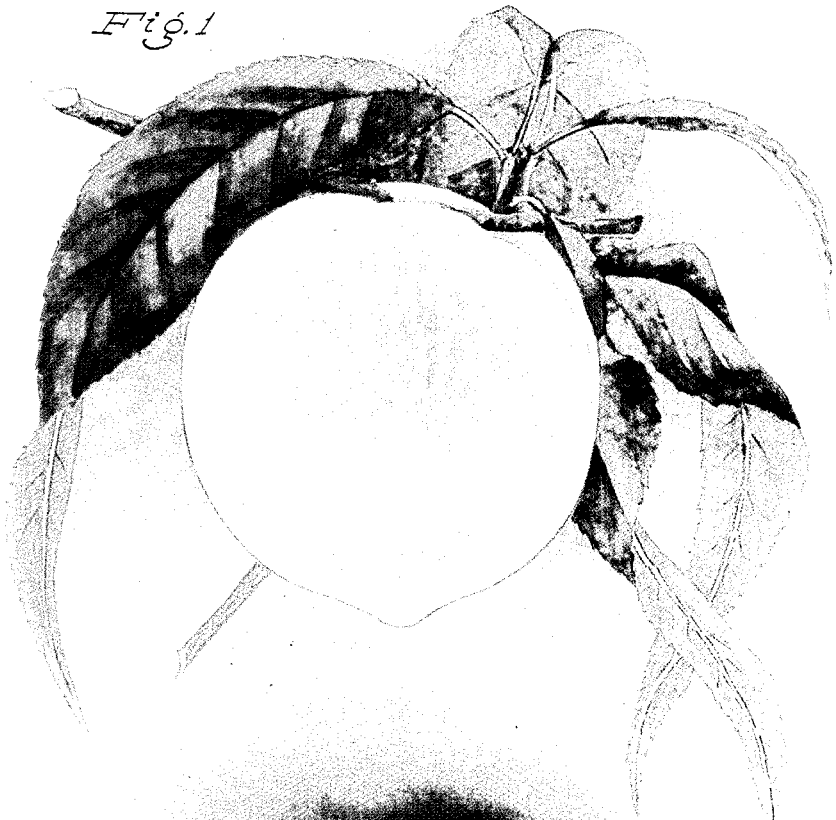
Fig. 1 is an elevation of one of the fruit, together with twigs and leaves.
Figure 2:
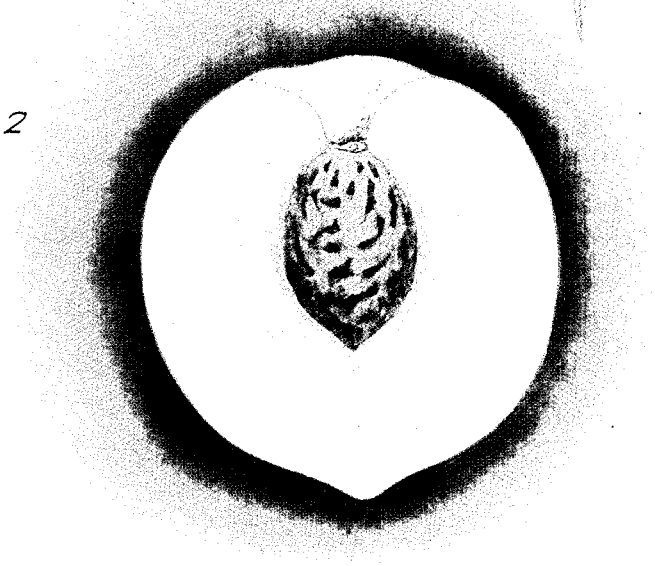
Fig. 2 is a sectional elevation of one of the fruit, with the stone exposed.

Referring now more specifically to the pomological details of this new and distinct variety of peach tree, the following is an outline description thereof; all major color plate identification being by reference to Maerz and Paul Dictionary of Color:

Tree:
- *Size.*—Medium.

- *Vigor.*—Medium.
- *Growth.*—Medium upright. Normally pruned to vase form.
- *Production.*—Productive.
- *Bearing.*—Regular bearer.

Trunk:
- *Size.*—Medium stocky.
- *Surface.*—Medium shaggy.

Branches:
- *Size.*—Medium stocky.
- *Surface.*—Medium shaggy.
- *Color.*—Reddish brown.
- *Lenticels.*—Medium size. Number—numerous to medium.

Leaves:
- *Size.*—Medium. Average length—5″ to 7″. Average width—1″ to 1¾″.
- *Form.*—Lanceolate; tip acuminate.
- *Thickness.*—Medium.
- *Surface.*—Smooth, except some rugose condition along midrib.
- *Margin.*—Crenate.
- *Petiole.*—Medium length; medium thickness.
- *Glands.*—None to seven, mostly two and three. Opposite. Medium small. Reniform. Brown to green. On base of the leaves and upper part of the petiole.
- *Stipules.*—On new growth, falling off early.
- *Color.*—Top side—medium green (22–L–8). Under side—lighter green (22–H–6). Midrib on under side yellowish green (18–K–1).

Flower buds:
- *Size.*—Medium.
- *Length.*—Medium.
- *Form.*—Plump; free.
- *Pubescence.*—Pubescent.

Flowers:
- *Blooming period.*—Midseason compared with other varieties.
- *Date of first bloom.*—March 4, 1954.
- *Date of full bloom.*—March 12, 1954.
- *Size.*—Medium.
- *Color.*—Pink.
- *Pollen.*—Present.

Fruit:
- *Maturity when described.*—Eating ripe.
- *Date of first picking.*—October 1, 1954.
- *Date of last picking.*—October 11, 1954.
- *Size.*—Relatively uniform. Large. Average diameter axially—2½″ to 3½″. Average transversely in suture plane—2¾″ to 3¾″. Average cheek to cheek—2¾″ to 3⅞″.
- *Form.*—Globose. Truncate at stem end. Slightly cuspidate at the apex on some specimens.
- *Suture.*—Distinct; shallow. Extends from base to apex, and slightly beyond. Slight depression beyond pistil point.
- *Ventral surface.*—Rounded; lips equal to sometimes unequal.
- *Cavity.*—Round to slightly elongated in suture plane, with suture showing on both sides. Average depth—⅜″ to ½″. Average breadth—1″. Markings—yellow, with red on many.
- *Base.*—Truncate.
- *Apex.*—Short.
- *Pistil point.*—Apical.

Skin:
- *Texture.*—Medium thick; medium tough; fairly tenacious to flesh.
- *Tendency to crack.*—None.
- *Down.*—Scant.
- *Color.*—Yellow under-color (9–I–4), shading to darker yellow (9–J–10), with one-fourth to one-half of the fruit having a red blush (3–L–11), somewhat mottled and streaked with darker red (5–L–12).

Flesh:

*Surface of pit cavity.*—Yellow to brownish, with some red showing. Pink fibers, with a few brownish fibers.

*Amygdalin.*—Moderate.

*Juice.*—Unusually juicy for a late ripening peach.

*Texture.*—Firm; meaty. Little mealiness when eating ripe.

*Fibers.*—Moderate; tender.

*Ripens.*—Evenly.

*Flavor.*—Sub-acid to mild.

*Aroma.*—Distinct.

*Eating quality.*—Good.

*Color.*—Bright yellow (9–K–3), shading to darker yellow (9–L–6) near the skin, mottled and streaked to a substantial extent with red (1–D–10 shading to 1–K–10) near stone.

Stone:

*Type.*—Free.

*Adherence.*—Some flesh adheres to the stem end on ventral edge in some specimens.

*Fibers.*—Long.

*Size.*—Medium. Average length—1½″ to 1¾″. Average breadth—1⅛″ to 1¼″. Average thickness—¾″ to 1″.

*Form.*—Obovate. Tip acuminate.

*Hilum.*—Oval.

*Apex.*—Acuminate.

*Sides.*—Unequal to equal.

*Surface.*—Irregularly furrowed toward apex. Pitted toward base.

*Ridges.*—Rounded toward apex; on either side; continuous.

*Pits.*—Elongated.

*Ventral edge.*—Medium thick.

*Dorsal edge.*—Narrow, shallow groove in center.

*Tendency to split.*—Slight.

*Color.*—Reddish brown (7–J–11).

Use: Market; local; dessert; canning; freezing.

Keeping quality: Good.

Shipping quality: Excellent.

The tree and its fruit herein described may vary in slight detail due to climatic and soil conditions under which the variety may be grown, and the method of growing, including pruning and thinning.

The following is claimed:

A new and distinct variety of peach tree, substantially as illustrated and described, which is of moderate vigor, and a regular bearer of large freestone fruit having yellow skin with a red blush and yellow flesh mottled and streaked with red next to the stone; characterized by a relatively late ripening period of the fruit; further characterized—in comparison to the Merrill Fiesta peach—by ripening usually about twenty days later but having somewhat less exterior color; and—additionally characterized—in comparison to the Elberta peach—by ripening usually about sixty days later; the fruit sizing easily, being relatively juicy, firm and meaty—with little mealiness when eating ripe—sub-acid to mild in flavor, of excellent shipping quality, and not darkening upon exposure to air.

No references cited.